(12) United States Patent
Cho et al.

(10) Patent No.: US 9,526,717 B2
(45) Date of Patent: Dec. 27, 2016

(54) COMPOSITION FOR TREATING IMMUNE DISEASES CONTAINING DAURINOL COMPOUND AS ACTIVE INGREDIENT

(71) Applicant: THE CATHOLIC UNIVERSITY OF KOREA INDUSTRY-ACADEMIC COOPERATION FOUNDATION, Seoul (KR)

(72) Inventors: Mi-La Cho, Seoul (KR); Dong-Yun Shin, Seoul (KR); Min-Jung Park, Incheon (KR); Seon-Yeong Lee, Gyeonggi-do (KR); Eun Ji Yang, Seoul (KR); Eun Kyung Kim, Seoul (KR); Hye-Jin Son, Seoul (KR); Eun-Jung Lee, Gyeonggi-do (KR); Jae-Kyung Kim, Chungcheongnam-do (KR); Sung-Hee Lee, Seoul (KR)

(73) Assignee: THE CATHOLIC UNIVERSITY OF KOREA INDUSTRY-ACADEMIC COOPERATION FOUNDATION, CATHOLIC UNIV. OF KOREA SONGEUI CAMPUS, Seoul (KR)

( * ) Notice: Subject to any disclaimer, the term of this patent is extended or adjusted under 35 U.S.C. 154(b) by 0 days.

(21) Appl. No.: 14/913,082

(22) PCT Filed: Aug. 22, 2014

(86) PCT No.: PCT/KR2014/007848
§ 371 (c)(1),
(2) Date: Feb. 19, 2016

(87) PCT Pub. No.: WO2015/026205
PCT Pub. Date: Feb. 26, 2015

(65) Prior Publication Data
US 2016/0193180 A1 Jul. 7, 2016

(30) Foreign Application Priority Data

Aug. 22, 2013 (KR) .................. 10-2013-0099546
Aug. 21, 2014 (KR) .................. 10-2014-0109203

(51) Int. Cl.
*A61K 31/365* (2006.01)
*A61K 36/75* (2006.01)

(52) U.S. Cl.
CPC ............. *A61K 31/365* (2013.01); *A61K 36/75* (2013.01)

(58) Field of Classification Search
CPC .............................. A61K 31/365; A61K 36/75
USPC .......................................................... 514/464
See application file for complete search history.

(56) References Cited

U.S. PATENT DOCUMENTS 5,627,195 A    5/1997  Hu
8,227,512 B2 *  7/2012  Nho .................. A61K 31/343
                                                         435/375

FOREIGN PATENT DOCUMENTS

JP       2013053077       3/2013
KR        100861320      10/2008

OTHER PUBLICATIONS

Al-Yahya, Mohammad A. et al., "New Alkaloids from Haplophyllum Tuberculatum," J. of Natural Products 55 (7):899-903, Jul. 1992.
Kang, Kyungsu et al., "A Novel Topoisomerase Inhibitor, Daurinol, Suppresses Growth of HCT116 Cells with Low Hematological Toxicity Compared to Etoposide," Neoplasia 13(11):1043-1057, Nov. 2011.
Paul Anastas and Robert Stevenson "Synthesis of Natural Lignan Arylnaphthalene Lactones, Daurinol and Retrochinensin," J. of Natural Products 54(6):1687-1691, Nov.-Dec. 1991.

* cited by examiner

*Primary Examiner* — Yevegeny Valenrod
(74) *Attorney, Agent, or Firm* — Joseph Hyosuk Kim; JHK Law

(57) ABSTRACT

The daurinol compound according to the present invention exhibits excellent therapeutic effects on arthritis and inflammatory bowel diseases by having an excellent activity in inhibiting the generation of IL-17 and TNF-α, which are inflammatory cytokines causing inflammation, and can alleviate transplant rejection by inhibiting the proliferation of alloreactive T cells and increasing regulatory T cells; therefore, the daurinol compound according to the present invention can be used as a pharmaceutical composition capable of treating and preventing immune diseases. In addition, being a natural substance derived from the Mongolian medicinal plant *Haplophyllum dauricum* or *Haplophyllum cappadocicum*, the daurinol compound according to the present invention does not cause cytotoxicity and thus may be used as a composition for a functional health food capable of preventing and remedying immune diseases.

7 Claims, 16 Drawing Sheets

A. Control of production of inflammatory cytokines

B. Effect of simultaneous control of Th17 inhibition/Treg cell induction

FIG. 13A  FIG. 13B  FIG. 13C
A. Weight
B. Disease activity index
C. Length of intenstine
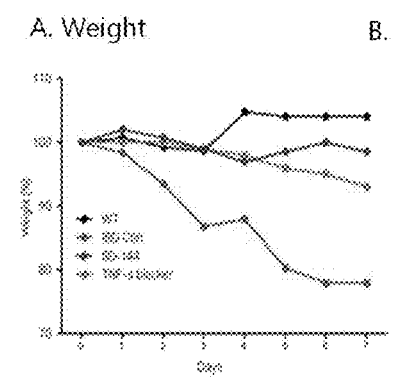
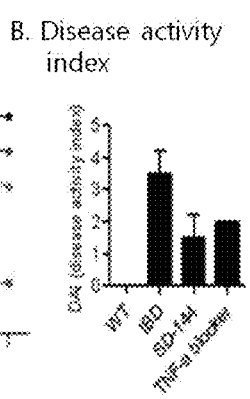
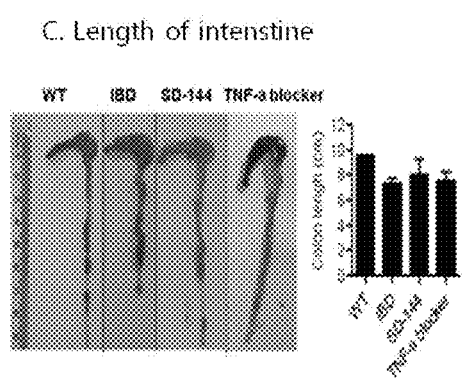
D. Staining of intestinal tissue
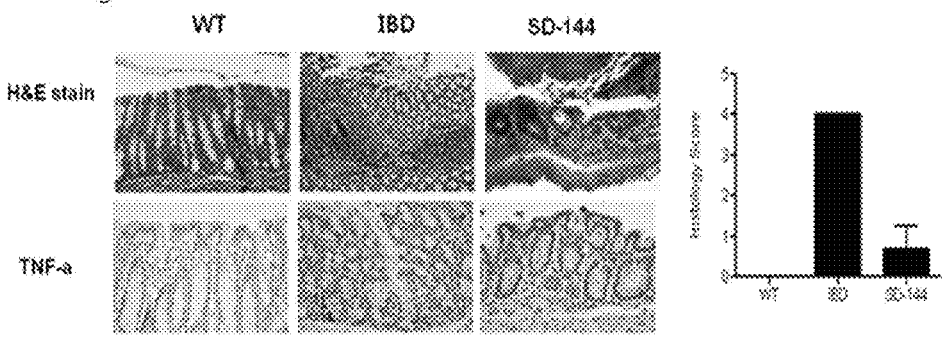
FIG. 13D FIG. 14A
FIG. 14B
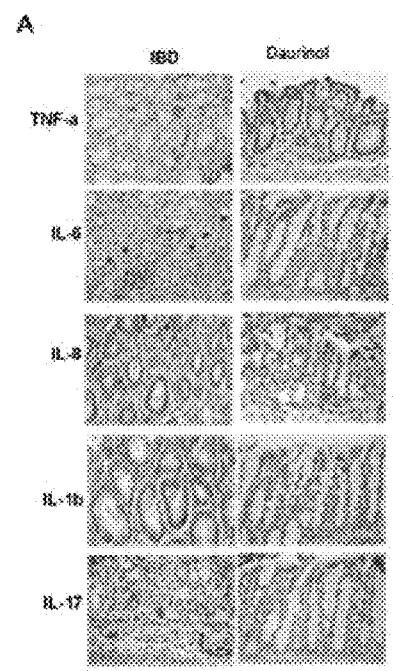
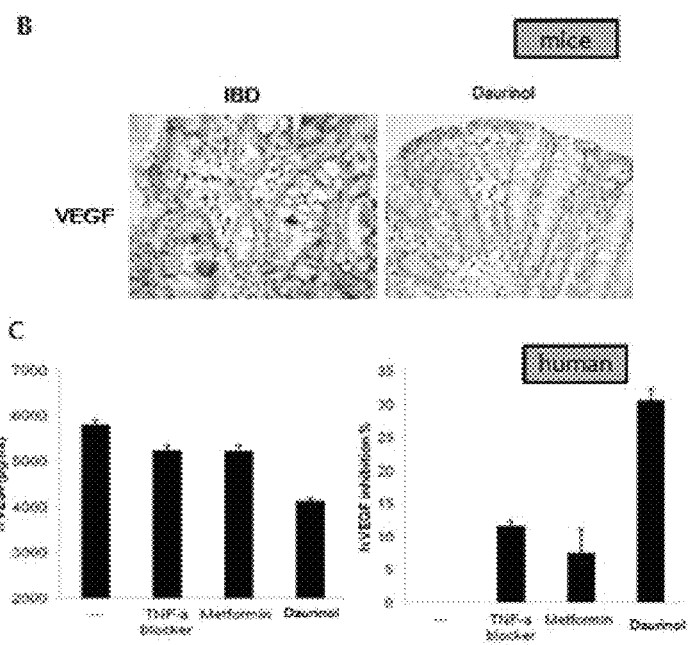
FIG. 14C FIG. 16A
FIG. 16B
A. Control of immune response of autoantibody production
B. Control of production of inflammatory cytokines
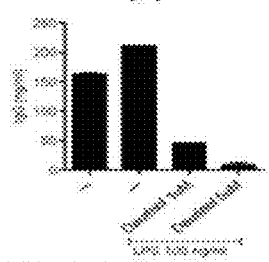
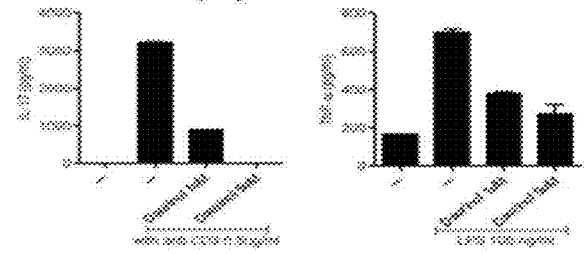
C. Effect of simultaneous control of th17 inhibition/treg cell induction
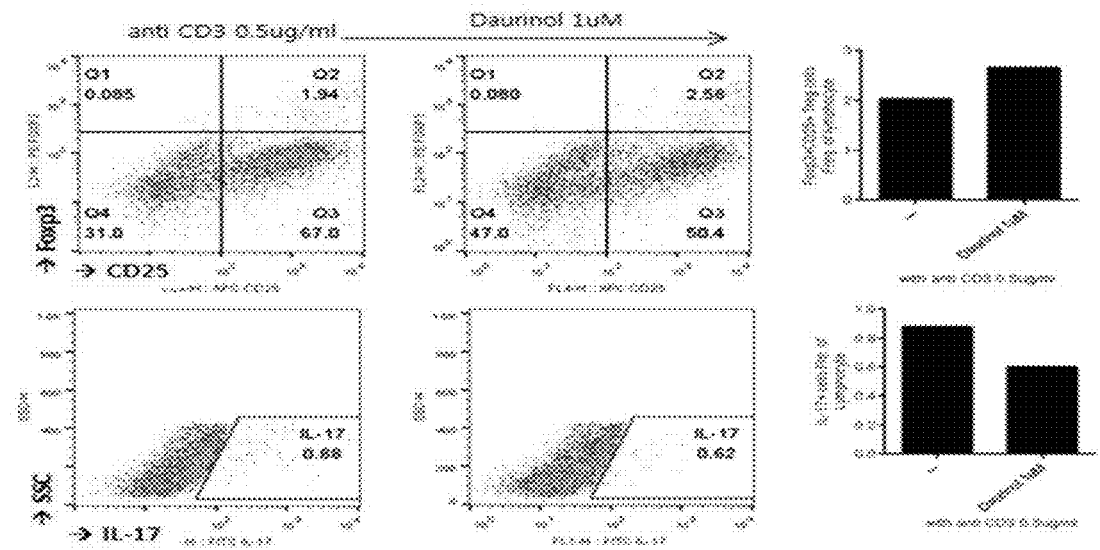
FIG. 16C

COMPOSITION FOR TREATING IMMUNE DISEASES CONTAINING DAURINOL COMPOUND AS ACTIVE INGREDIENT

TECHNICAL FIELD

The present invention relates to a daurinol compound for effectively preventing and treating immune diseases and uses thereof.

BACKGROUND ART

The immune system plays a role in protecting human body from antigens, which are harmful foreign materials. Examples of the antigens may include bacteria, viruses, toxic materials, cancer cells, and blood or tissues of other people or animals. The immune system produces antibodies to respond to and remove these harmful materials. However, when the immune system does not function properly, the immune system cannot distinguish normal health organs of its own from harmful foreign antigens thereby destroying normal tissues, which is called autoimmune disease. In the case of an autoimmune disease, normal tissues are also included in the reaction target. The cause of autoimmune disease is still not clear but there is a theory assuming that microorganisms such as bacteria or drugs may cause autoimmune diseases in those who are specifically inherited with these genes and are thus vulnerable to autoimmune diseases.

Various chemical and biological immune therapies have been developed for the treatment of autoimmune diseases. The typical method of treatment is to deteriorate the overall immune response of the body using a chemical agent such as steroids or an anti-immune cell antibody, for example, to deteriorate the entire immune response of the body including the normal functions of B cells by administering CD22, CD20, CD19, CD74, or antibodies that bind to HLA-DR.

Korean Patent Application Publication No. 2008-0109705 relates to mesenchymal stem cell-mediated autologous dendritic cells with increased immunosuppression, and it discloses dendritic cells with improved T-cell immunosuppression and uses thereof for the treatment of autoimmune diseases.

U.S. Pat. No. 7,074,403 relates to immunotherapy of autoimmune disorders using antibodies which target B-cells, and it discloses antibodies which bind specifically to B-cell antigens.

U.S. Pat. No. 7,473,592 relates to a cell composition for the treatment of immune diseases using a different object, and it discloses T cell composition coated with anti-CD3 and anti-CD28 antibodies.

The traditional methods for treating autoimmune diseases are largely classified into steroid agents and immunosuppressants. However, these methods deteriorate the overall immune system of the body when they are administered for a long period of time, and they thus weaken the overall immune functions to respond to foreign invasion thereby causing side effects, such as, occurring other diseases. Additionally, steroid agents have the side effects of causing systemic dermatitis.

Through the endeavors to discover suitable drugs and methods by screening therapeutic methods for treating autoimmune diseases, the treatment of autoimmune diseases is mainly based on the use of immunosuppressant drags, such as glucocorticoids, calcineurin inhibitors, and antiproliferatives-antimetabolites. However, since these pharmacological therapies act on a variety of targets, they may reduce the immune functions as a whole, or they may have the disadvantage of having different cytotoxic effects due to a long-term use, and thus suppress the immune system in a non-specific way, thereby exposing patients to a risk of infections and cancer. Since calcineurin and glucocorticoids exhibit an additional disadvantage due to their nephrotoxicity and diabetogenic effects, their uses in several clinical conditions (for example, renal insufficiency, diabetes, and the like) are limited.

For these reasons, patients with immune diseases including autoimmune diseases have had a great interest in therapeutic types considered as "natural", which have a weak anti-inflammatory effect but with no major adverse effects and can be used as prevention and auxiliary treatment of diseases, and many researchers have a growing interest in the development of nature-derived therapeutic agents.

In this regard, for the development of stable therapeutic agents with less adverse effects, studies have been recently focused on natural materials. Prior arts as such, Korean Patent No. 668067 discloses that phenylbutenoid derivatives isolated from ginger have excellent anti-inflammatory effect, and Korean Patent No. 396526 discloses that xanthorrhizol isolated from *Curcuma xanthorrhiza Roxb.* has an anti-inflammatory effect and thus can be used for the treatment of inflammations.

Meanwhile, daurinol, an arylnaphthalene lignan, is a single chemical component, which was first isolated from *Haplophyllum dauricum*, the medicinal plant of Mongolia, by the present inventors in early 1980s. The daurinol was also isolated from *Haplophyllum cappadocicum*, the same family but a different plant (Batsuren D, et al., Chemistry of Natural Compounds, 17, 223-225, 1982; Gozler B, et al., Phytochemistry, 31, 2473-2475, 1992). However, its pharmacological effect has never been reported yet. *Haplophyllum* sp. plants are perennial grasses and widely spread in central Asia. They have been used for the traditional folk remedy for various diseases over hundreds of years.

Under these circumstances, the present inventors have discovered that a daurinol compound has the effect of inhibiting the production of IL-17 and TNF-α, which are inflammation inducing materials, and thus it can be used as a therapeutic agent for treating immune diseases, thereby completing the present invention.

DISCLOSURE

Technical Problem

The present invention is directed to providing a pharmaceutical composition for preventing and treating immune diseases containing a daurinol compound as an active ingredient.

The present invention is directed to providing a health functional food composition for preventing and improving immune diseases containing a daurinol compound as an active ingredient.

The present invention is also directed to providing a method for preventing and treating immune diseases comprising administering to a patient in need thereof an effective amount of daurinol compound.

Technical Solution

In order to achieve the above objects, one aspect of the present invention provides a pharmaceutical composition for preventing and treating immune diseases including daurinol represented by the following Formula 1 as an active ingredient:

[Formula 1]

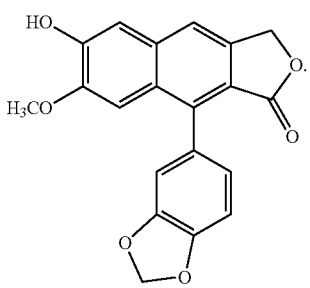

In an exemplary embodiment of the present invention, the immune diseases may be selected from the group consisting of osteoarthritis, rheumatoid arthritis, asthma, dermatitis, psoriasis, cystic fibrosis, post transplantation late and chronic solid organ rejection, multiple sclerosis, systemic lupus erythematosus, Sjogren syndrome, Hashimoto thyroiditis, polymyositis, scleroderma, Addison disease, vitiligo, pernicious anemia, glomerulonephritis, pulmonary fibrosis, inflammatory bowel disease, Crohn's disease, autoimmune diabetes, diabetic retinopathy, rhinitis, ischemia-reperfusion injury, post-angioplasty restenosis, chronic obstructive pulmonary diseases (COPD), Graves' disease, gastrointestinal allergy, conjunctivitis, atherosclerosis, coronary artery disease, angina, cancer metastasis, small artery disease, and mitochondrial disease.

In another exemplary embodiment of the present invention, daurinol may be separated from an extract of a plant belonging to *Haplophyllum* species.

In still another exemplary embodiment of the present invention, the composition may exhibit a therapeutic effect by controlling the secretion of inflammatory cytokines.

In still another exemplary embodiment of the present invention, the inflammatory cytokines may be IL-17 or TNF-α.

In still another exemplary embodiment of the present invention, the composition may exhibit one or more effect selected from inhibition of the differentiation of osteoclasts, reduction of intraarticular inflammation, reduction of osetoclasiaand reduction of cartilage damage.

In still another exemplary embodiment of the present invention, the composition may exhibit one or more effect selected from inhibition of proliferation of alloreactive T cells and increase of expression of Regulatory T cells (Treg).

In still another exemplary embodiment of the present invention, there is provided a health functional food composition for preventing and improving immune diseases including daurinol represented by the following Formula 1 as an active ingredient:

[Formula 1]

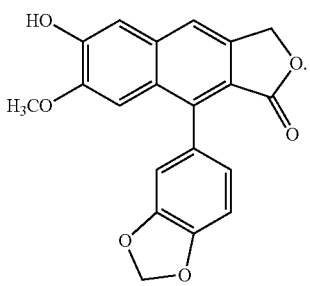

In order to achieve the above objects, one aspect of the present invention provides a method for preventing and treating immune diseases comprising administering to a patient in need thereof an effective amount of daurinol compound.

Advantageous Effects

The daurinol compound according to the present invention exhibits excellent therapeutic effects on arthritis and inflammatory bowel diseases by having excellent activity in inhibiting the generation of inflammatory cytokines causing inflammation, and can alleviate transplant rejection by inhibiting the proliferation of alloreactive T cells and increasing regulatory T cells. Accordingly, the daurinol compound according to the present invention can be used as a pharmaceutical composition capable of treating and preventing immune diseases. In addition, being a natural substance derived from the Mongolian medicinal plant *Haplophyllum dauricum* or *Haplophyllum cappadocicum*, the daurinol compound according to the present invention does not cause cytotoxicity and thus may be used as a composition for a functional health food capable of preventing and improving immune diseases.

DESCRIPTION OF DRAWINGS

FIGS. 13A, 13B, 13C and 13D illustrate the observed results of the effects of daurinol treatment on the changes in weight (A), disease activity index (B), and length of intestine (C), and the result of hematoxylin and eosin (H&E) staining for the investigation of the presence of reduction in the destruction of intestinal tissues by daurinol treatment (D), in an animal model with inflammatory bowel disease.

FIGS. 14A, 14B and 14C illustrate the measurement results of the effects of daurinol treatment on the change in expression (A) of TNF-α, IL-6, IL-8, IL-1b, and IL-17, which are inflammatory cytokines in intestinal tissues, and on the changes in the expression of mouse- and human VEGF (B and C).

FIGS. 16A, 16B and 16C illustrate the measurement results of the effects of daurinol treatment on the inhibition of IgG antibody production (A), the inhibition of expression of IL-17 and TNF-α inflammatory cytokines (B), and the control of activity of Th17/Treg cells (C), in an animal model with lupus.

MODES OF THE INVENTION

The present invention is characterized in that it provides a novel use of a daurinol compound isolated from a natural material as a novel therapeutic agent for the treatment of immune diseases with excellent anti-inflammatory activity without causing any cytotoxicity in vivo.

The daurinol of the present invention is a single chemical component of an arylnaphthalene lignan derived from *Haplophyllum dauricum* or *Haplophyllum cappadocicum*, which are the medicinal plants of Mongolia, and represented by the following Formula 1.

[Formula 1]

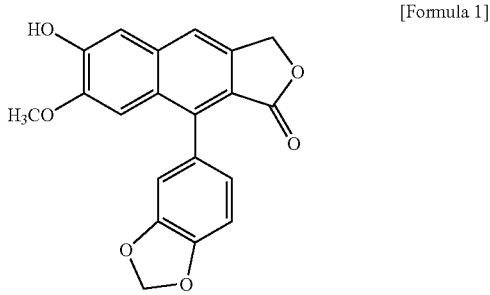 [SMILES: COc1cc2c(-c3ccc4c(c3)OCO4)c3c(cc2cc1O)COC3=O]

The *Haplophyllum dauricum* (L.) G. Don. can be collected from Uvurkhangaiskii aimak province of Mongolia, can be extracted using ethanol as a solvent. Daurinol is present in abundant in the aerial part of the plants but may also be isolated from their roots. The extract may be fractionated using petroleum ether, chloroform, ethyl acetate, or butanol, and among them, the chloroform fraction may be separated using a silica gel column (1:10), and may be eluted using a benzene-chloroform solvent at various ratios. Meanwhile, daurinol may be separated via fractional recrystallization using methanol as a solvent.

The daurinol of the present invention may be extracted from a particular plant belonging to *Haplophyllum* sp. such as *Haplophyllum dauricum* and *Haplophyllum cappadocicum*, or may be prepared using a chemical synthetic method well known in the art.

The present inventors have confirmed that a daurinol compound has excellent anti-inflammatory effect and thus they can be used as a therapeutic agent for the treatment of immune diseases, and in an exemplary embodiment of the present invention, a daurinol compound was exhibited to inhibit the expression of IL-17 and TNF-α, which are inflammatory cytokines, thus exhibiting the effects of preventing and treating immune diseases (refer to FIG. 7).

Figure 2:
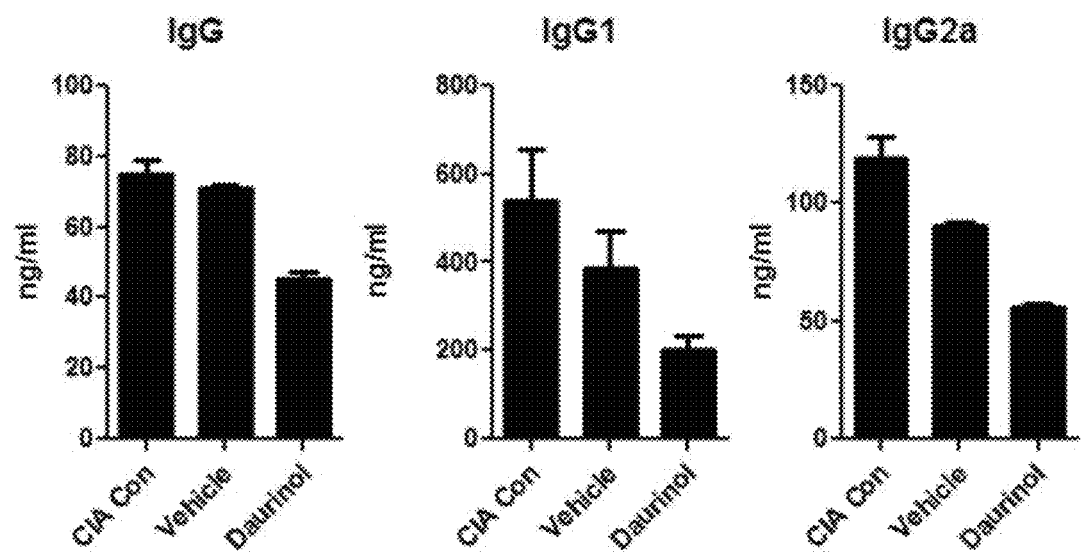
FIG. 2 illustrates the measurement results of IgG amount in serum after administration of daurinol in an animal model with arthritis.
Figure 3:
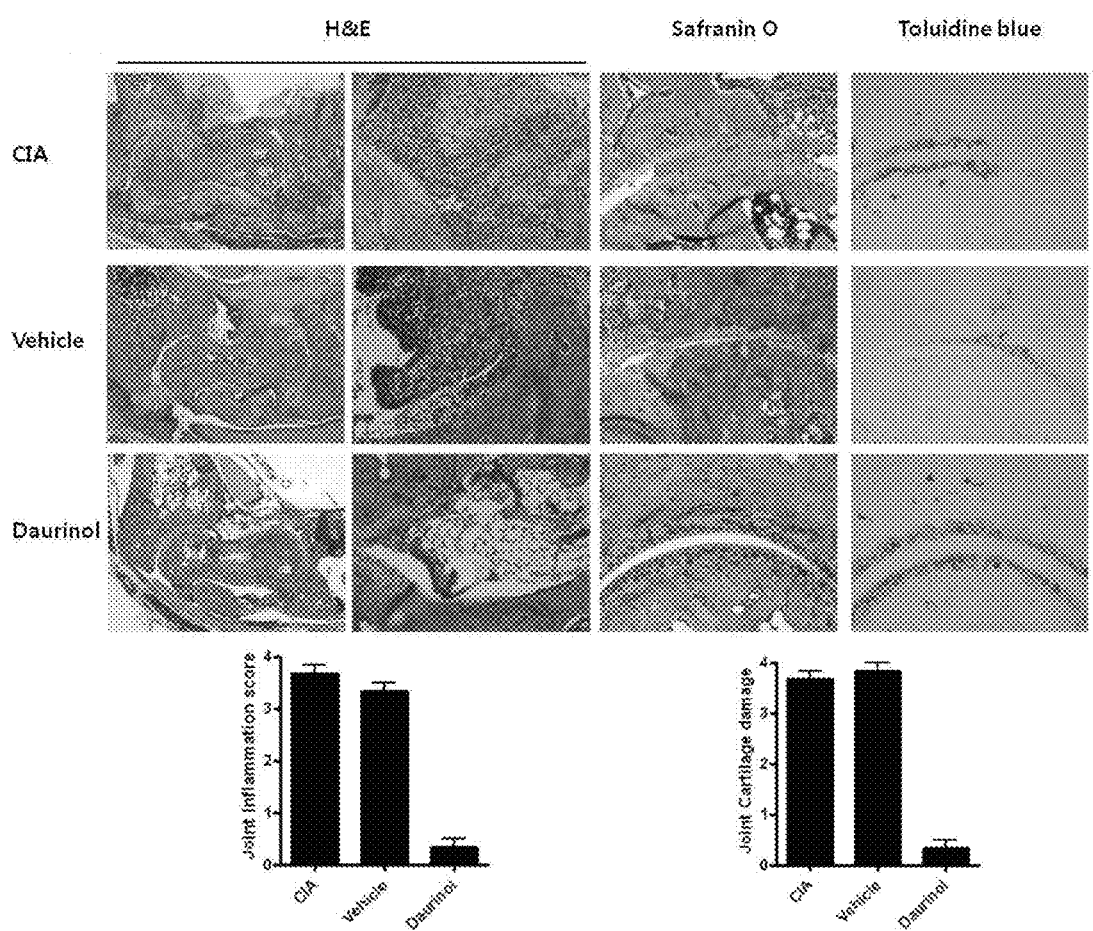
FIG. 3 illustrates the results of the degree of intraarticular inflammation, osteoclasia, and cartilage injury observed via tissue staining after administration of daurinol in an animal model with arthritis.

Additionally, it was confirmed in an evaluation of arthritis index that the administration of the daurinol compound of the present invention to an animal model with arthritis exhibited a significant decrease in arthritis (refer to FIG. 1), a significant decrease in IgG, IgG1, and IgG2a in the serum of arthritis animals (refer to FIG. 2), and a significant decrease in intraarticular inflammation, osteoclasia, and cartilage injury in an animal model (refer to FIG. 3). Meanwhile, it was confirmed in an in vitro experiment that the daurinol treatment could significantly inhibit the differentiation of bone marrow cells into osteoclasts (refer to FIG. 5).

Figure 10:
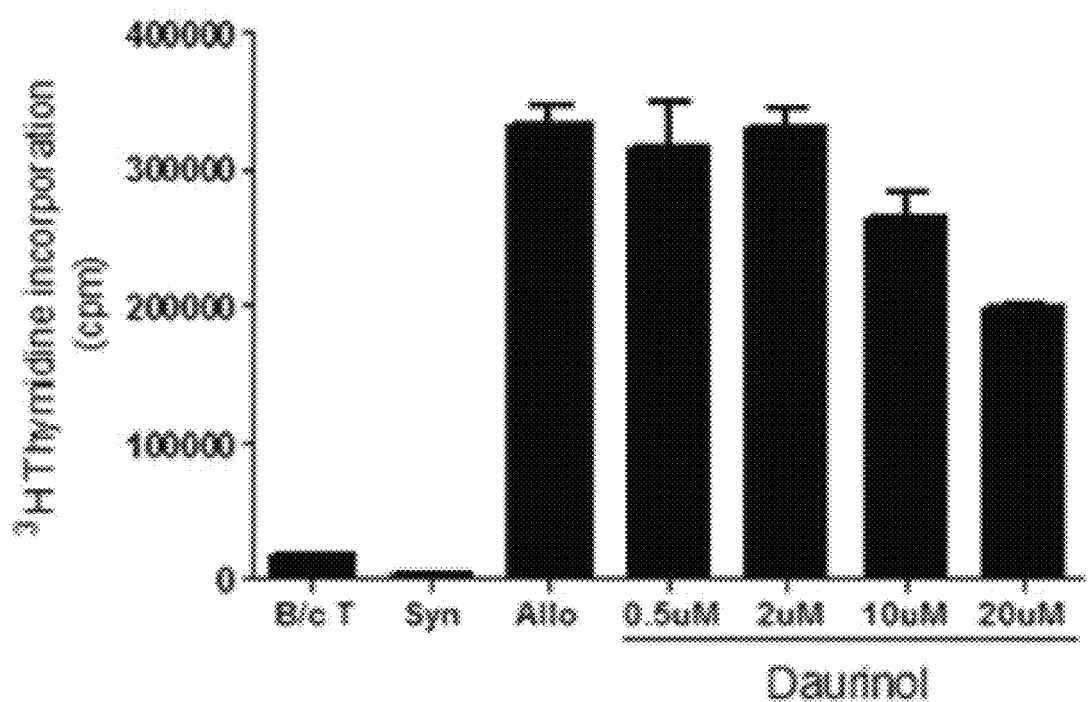
FIG. 10 illustrates the results of the effect of in vitro daurinol treatment on the inhibition of proliferation of T cells involved in rejection after transplantation.
Figure 11:
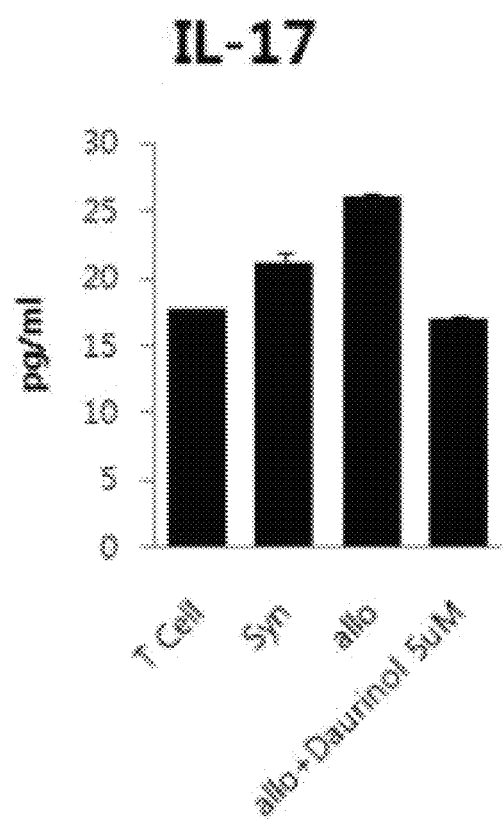
FIG. 11 illustrates the results of the effect of in vitro daurinol treatment on the inhibition of production of IL-17 involved in rejection after transplantation.
Figure 12:
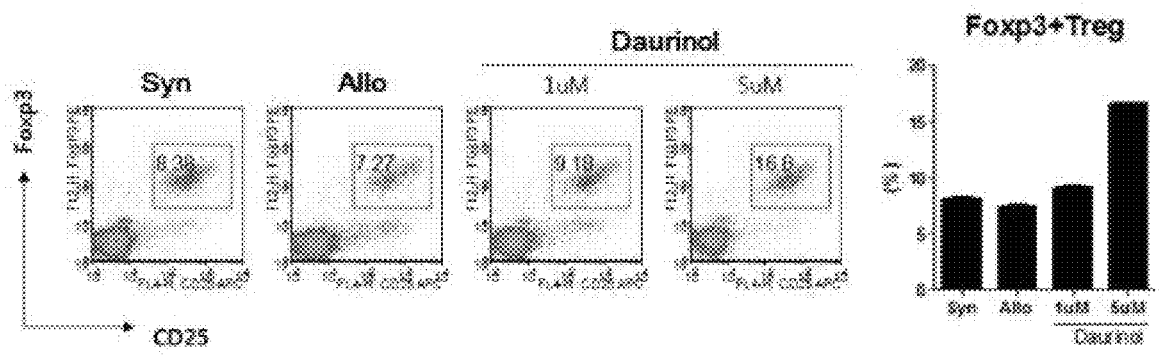
FIG. 12 illustrates the results of the effect of in vitro daurinol treatment on the proliferation of regulatory T cells (Treg) involved in rejection after transplantation.

The composition of the present invention was also exhibited to exhibit an inhibitory effect against the rejection after transplantation, that is, the experimental group treated with the composition including daurinol exhibited an inhibition of the proliferation of alloreactive T cells (refer to FIG. 10), an inhibition of IL-17 production (refer to FIG. 11), and an increase in the proliferation of regulatory T cells (refer to FIG. 12).

Additionally, it was observed in an animal model with inflammatory bowel disease that the treatment of the composition of the present invention improved the weight decrease of the animal model, significantly reduced the disease activity index (DAI), and maintained the length of the intestine to a level similar to that of normal control group (refer to FIG. 13).

Accordingly, the composition of the present invention can be used for the prevention or treatment of immune diseases.

Specifically, the immune diseases may be those diseases which are resulted from the overproduction of IL-17 and TNF-α, which are inflammatory cytokines.

More specifically, the immune diseases may include osteoarthritis, rheumatoid arthritis, asthma, dermatitis, psoriasis, cystic fibrosis, post transplantation late and chronic solid organ rejection, multiple sclerosis, systemic lupus erythematosus, Sjogren syndrome, Hashimoto thyroiditis, polymyositis, scleroderma, Addison disease, vitiligo, pernicious anemia, glomerulonephritis, pulmonary fibrosis, inflammatory bowel disease, Crohn's disease, autoimmune diabetes, diabetic retinopathy, rhinitis, ischemia-reperfusion injury, post-angioplasty restenosis, chronic obstructive pulmonary diseases (COPD), Graves' disease, gastrointestinal allergy, conjunctivitis, atherosclerosis, coronary artery disease, angina, cancer metastasis, small artery disease, mitochondrial disease, and the like.

More preferably, examples of the autoimmune diseases may include i) rheumatoid arthritis in which the body's immune system attacks tissues of various joints, ii) inflammatory bowel disease in which the body's immune system attacks the intestine, and iii) graft rejection, which causes an immune response based on cell-mediated immunity occurring after the transplantation of genetically different cells, tissues, and organs; destruction of transplanted tissues, and excretion of graft.

Based on the experimental results according to the present invention exhibiting the therapeutic effects for the treatment of immune diseases described above, the present invention can provide a pharmaceutical composition for preventing and treating immune diseases including daurinol as an active ingredient.

Additionally, the daurinol compound according to the present invention may be used in the form of a salt, and preferably in the form of a pharmaceutically acceptable salt. Examples of the salt may be preferably an acid addition salt formed by a pharmaceutically acceptable free acid, and as the free acid, an organic acid and an inorganic acid may be used. Examples of the organic acid may include citric acid, acetic acid, lactic acid, tartaric acid, maleic acid, fumaric acid, formic acid, propionic acid, oxalic acid, trifluoroacetic acid, benzoic acid, gluconic acid, methanesulfonic acid, glycolic acid, succinic acid, 4-toluenesulfonic acid, glutamic acid, and aspartic acid, although not limited thereto. Additionally, examples of the inorganic acid may include hydrochloric acid, bromic acid, sulfuric acid, and phosphoric acid, although not limited thereto.

Additionally, the composition of the present invention may include a pharmaceutically effective amount of the daurinol compound alone, or may further include one or more pharmaceutically acceptable carrier, excipient, or diluent. As used herein, the term "pharmaceutically effective amount" refers to an amount sufficient for the prevention, improvement, and treatment of the symptoms of immune diseases, and the daurinol compound may be included in a concentration of from 5 $\mu$M to 25 $\mu$M, relative to the composition, or in an amount of from 0.01 wt % to 70 wt %, relative to the total weight of the composition.

Additionally, the pharmaceutically effective amount of the daurinol compound according to the present invention is in the range from 0.5 mg/day to 100 mg/day per kg of weight, and preferably, 0.5 mg/day to 10 mg/day per kg of weight. However, the pharmaceutically effective amount may be appropriately changed according to the severity of symptoms, the patient's age, weight, health conditions, sex, administration route, duration of administration, and the like.

Additionally, as used herein, the term "pharmaceutically acceptable" refers to a composition which is physiologically acceptable and generally does not cause allergic actions, such as gastrointestinal disorder and dizziness, or any similar response thereof, when administered to humans. Examples of the carrier, excipient, and diluent may include lactose, dextrose, sucrose, sorbitol, mannitol, xylitol, erythritol, maltitol, starch, acacia rubber, alginate, gelatin, calcium phosphate, calcium silicate, cellulose, methyl cellulose, polyvinylpyrrolidone, water, methyl hydroxybenzoate, propyl hydroxybenzoate, talc, magnesium stearate, mineral oil, and the like. Additionally, the composition may further contain a filler, an anti-coagulant, a lubricant, a humectant, a flavoring agent, a preservative, and the like Additionally, a filler, an anti-aggregating agent, a lubricant, a humectant, a flavoring agent, an emulsifying agent, a preservative, and the like, may be further included.

Additionally, the composition of the present invention may be formulated using a method known in the art for providing a rapid, sustained, or delayed release of an active ingredient. The formulation type may be in the form of powders, granules, tablets, emulsions, syrups, aerosols, soft or hard gelatin capsules, sterile injection solutions, sterile powders, and the like.

The composition of the present invention may be administered via various routes including oral, dermal, subcutaneous, intravenous, and intramuscular administrations, and the dose of the active ingredient may be appropriately selected according to various factors, such as administration route, the patient's age, sex, weight, and severity of illness, and the like. Additionally, the composition of the present invention for preventing and improving the symptoms of immune diseases may be administered in combination with a known compound having the effects of preventing, improving, or treating the symptoms of immune diseases.

Accordingly, the present invention provides a method for preventing and treating immune diseases comprising administering to a patient in need thereof an effective amount of daurinol compound.

Furthermore, the daurinol compound according to the present invention has safety because it does not cause any cytotoxicity or adverse effects and thus it can be safely used in vivo, and thus can be used as a food composition for preventing and improving immune diseases.

Accordingly, the food composition for preventing and improving immune diseases including the daurinol compound as an active ingredient can be easily used as a food, which is effective in preventing and improving the symptoms of immune diseases, for example, a main source or a subsidiary source of foods, a food additive, a functional food or beverage.

As used herein, the term "food" refers to a natural or processed food including one or more nutrient, preferably those which are in a state to be directly eaten after a certain degree of processing, and in a conventional meaning, refers to those including foods, food additives, functional foods and beverages.

Examples of the foods, to which the composition of the present invention for preventing and improving the symptoms of immune diseases, may include, for example, various kinds of foods, beverages, gums, teas, vitamin complexes, functional foods, and the like. Additionally, the foods of the present invention may include special nutrient foods (for example, milk formula, infant formula, and the like), processed meat products, fish meat products, soybean food products, starch jellies, noodles (for example, Ramens, fine noodles, and the like) breads, health supplementary foods, seasoning foods (for example, soy sauce, soybean paste, red pepper paste, mixed soybean paste, and the like), sauces, confectioneries (for example, snacks), candies, chocolates, gums, ice creams, dairy products (for example, fermented milk, cheese, and the like), other processed foods, Kimchi, pickled foods (various kinds of Kimchi, pickled vegetables, and the like), beverages (for example, fruit drinks, vegetable drinks, soybean milks, fermented drinks, and the like), natural seasonings (for example, ramen soups, and the like), but are not limited thereto. The foods, beverages, and food additives may be prepared according to the conventional methods.

Additionally, as used herein, the term "functional food" refers to a group of value added foods, which are prepared so that the functions of the foods can be acted on and expressed to comply with particular purposes by applying physical, biochemical, and biotechnological ways to food, or processed foods, which are designed and processed so that the foods can sufficiently express in vivo regarding the in vivo regulatory functions such as control of biodefense rhythm, prevention and recovery of diseases, and the like, and in particular, health functional foods. The functional foods may include sitologically acceptable food supplementary additives, and may further include suitable carriers, excipients, and diluents, which are conventionally used in the preparation of functional foods.

Additionally, as used herein, the term "beverage" collectively refers to any drink that can be served for the purposes of quenching thirst or enjoying tastes, and includes functional beverages. The beverages are not particularly limited regarding their ingredients, except that they include a composition for preventing and improving the symptoms of the immune diseases as an essential ingredient in an indicated ratio, and may further include various flavoring agents or natural carbohydrates, and the like, as additional ingredient as in the case of conventional beverages.

Furthermore, the foods of the present invention including the composition for preventing and improving the symptoms of immune diseases may include, in addition to the above ingredients, various nutrients, vitamins, minerals (electrolytes), flavoring agents such as synthetic and natural flavoring agents, color fixing agents, fillers (cheese, chocolates, and the like), pectic acid and salts thereof, alginic acid and salts thereof, organic acids, protective colloidal thickeners, pH controlling agents, stabilizers, preservatives, glycerine, alcohols, carbonating agents used in carbonate beverages, and these ingredients may be used alone or in combination.

In the foods including the composition for preventing and improving the symptoms of immune diseases, the composition according to the present invention may be included in an amount from 0.001 wt % to 90 wt % relative to the total weight of the food, and preferably 0.1 wt % to 40 wt %, and in the case of a beverage, the composition may be included in an amount from 0.001 g to 2 g based on 1000 mL, and preferably from 0.01 g to 0.1 g. However, when the food is ingested for a long period of time for the purpose of health and sanitation or for the control of health conditions, the content of the composition is not limited thereto but may be used in excess of the above ranges due to the safety of the active ingredients.

The present invention will be explained in further detail herein below with reference to Examples, however, they are disclosed for illustrative purposes and it should be obvious to one of ordinary skill in the art that they should not be construed as limiting the scope of the present invention.

EXAMPLE 1

Analysis of Therapeutic Effect of Daurinol on Arthritis

<1-1> Preparation of Experimental Animals

For experimental animals, 7-week-old male DBA/1J mice were used. For the preparation of an animal model with arthritis, type II collagen (CII, hereinafter) was dissolved in 0.1 N acetic acid solution to become 4 mg/ml dialyzed in dialysis buffer (50 mM Tris, 0.2 N NaCl), mixed with an equal amount of complete Freund's adjuvant (CFA, Chondrex) including *M. tuberculosis*, subcutaneously injected into the tail fundus of the mouse, and the immunogen was injected in an amount of 100 μL (i.e., 100 μL/100 μg) per mouse (primary injection). Two weeks thereafter, the same CII was mixed with an equal amount of incomplete Freud's adjuvant (IFA, Chondrex), and 100 μL (i.e., 100 μL/100 μg) of the mixture was injected into on the foot pad of a hind leg (secondary injection).

After the secondary immunization by a secondary injection, daurinol was injected intravenously three times daily in an amount of 20 mg/kg of weight for a total of 9 times, in which daurinol was used after dissolving in a mixed solvent, which was prepared by mixing DMSO:Crernophor EL:DW in a 1:1:8 ratio. Each group consisted of 5 mice and the evaluation on arthritis was performed until the $7^{th}$ week. Additionally, each experimental animal was sacrificed during the period when there was a significant difference in arthritis index for in vitro experiment, and the degree of disease activity of arthritis within blood and joint tissues and the therapeutic effect by daurinol were examined.

<1-2> Evaluation of Arthritis Index

With the first inoculation as the starting point, four observers, who were not aware of the details of the experiment, started to evaluate the severity of arthritis three times a week by observing from the $3^{rd}$ week thereafter until the $7^{th}$ week. In particular, the evaluation of arthritis was conducted as follows. The scores for each mouse rendered on the remaining three legs other than the leg, which was injected with the CII/CFA at the secondary injection, according to the following guideline were combined, divided by 3 to obtain a mean value, and again another mean value, which was obtained by combining the scores obtained by three observers in each animal model and divided thereafter, were used. The criteria and the scores for the evaluation of arthritis are as follows.

—Criteria for Evaluation—

0 point: no edema or swelling 1 point: slight edema and redness restricted to leg and ankle joint 2 points: slight edema and redness from ankle joint to metatarsal 3 points: moderate edema and redness from ankle joint to metatarsal 4 points: edema and redness from ankle to the entire leg In particular, the highest arthritis index for each mouse is 4 points, and thus the highest disease index for each mouse is 16.

Figure 1:
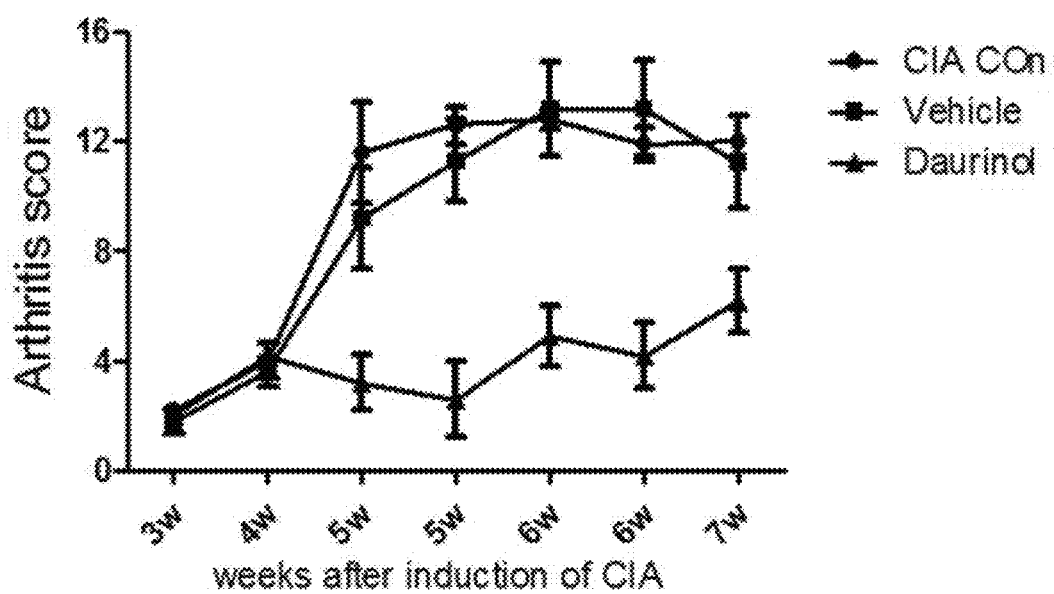
FIG. 1 illustrates a graph illustrating the evaluation results of arthritis index for determining the therapeutic effect of daurinol on treating rheumatoid arthritis in an animal model with arthritis.

As a result of the observation, it was found that the animal model with a collagen induced arthritis (CIA) exhibited a continued increase in arthritis index after the $4^{th}$ week thus indicating the aggravation of the arthritis, whereas the animal model injected with daurinol exhibited almost no increase in arthritis index (refer to FIG. 1).

<1-3> Measurement of IgG, IgG1, and IgG2a in the Serum

For the measurement of the change in the amount of IgG, IgG1, and IgG2a in the serum in a mouse model with collagen induced arthritis (CIA) by the injection of daurinol, the mouse injected with daurinol was euthanased three weeks after the daurinol injection, and its serum was collected and the expression levels of IgG, IgG1, and IgG2a were examined by sandwich ELISA. Monoclonal anti-IgG, anti-IgG1, and anti-IgG2 were allowed to react in a 96-well plate at a concentration of 2 g/mL at 4° C. overnight, and upon reaction, non-specific binding was blocked using a blocking solution (1% BSA/PBST). Commercial IgG, IgG1, and IgG2a in a half amount was continuously diluted and used as standards, and the supernatant of cell culture was reacted at room temperature for 2 hours. Then, the biotinylated secondary antibodies were reacted at room temperature for 2 hours, washed 4 times, and added with ExtraAvidin-alkaline phosphatase conjugate after dilution, and reacted at room temperature for 2 hours. Subsequently, PNPP/DEA solution was added thereto to fix color and absorbance was measured at 405 nm.

As a result, IgG, IgG1, and IgG2a were overexpressed in the case of a mouse model with arthritis, however, the expression of IgG was effectively reduced by daurinol treatment (refer to FIG. 2).

<1-4> Histological Examination

An animal model with collagen induced arthritis (CIA) was injected intravenously with daurinol, and three weeks thereafter, the experimental animal was euthanased. Then, the hind leg of the mouse was fixed with 10% formalin, and calcareous was removed from its bones, and coated with paraffin. Joint slices (7 μm) were prepared and stained with hematoxylin and eosin. Additionally, for the confirmation of the degree of cartilage damage, a histological examination was performed by staining with Toluidine blue and Safranin O.

As a result of histological examination, it was observed that numerous immune cells were infiltrated in the joints of the animal model with collagen induced arthritis, and pannus formation, cartilage destruction, and bone erosion, and the like. In contrast, the degree of destruction of joints and cartilage was not exhibited to be severe in the animal injected intravenously with daurinol (refer to FIG. 3).

<1-5> Measurement of Expression of Inflammatory Cytokines

An animal model with collagen induced arthritis (CIA) was injected intravenously with daurinol, and three weeks thereafter, the experimental animal was euthanased. Then, the hind leg of the mouse was fixed with 10% formalin, and calcareous was removed from its bones, and coated with paraffin. Joint slices (5 μm) were prepared and, before performing the basic staining, the joint slices went through deparaffinization process using xylene, and dipped into ethanol from high concentration to low concentration.

For the examination of expression of IL-17, IL-6, IL-1beta, and TNF-α, a nonspecific reaction was blocked by coating with 10% normal goat serum for 30 minutes, and after the progress of the reaction, anti-mouse IL-17, anti-mouse IL-6, anti-mouse IL-1beta, and anti-mouse TNF-α ab were coated on top of the tissues and cultured 4° C. overnight. Then, the resulting tissues were reacted with HRP for 2 hours and observed under a microscope.

Figure 4:
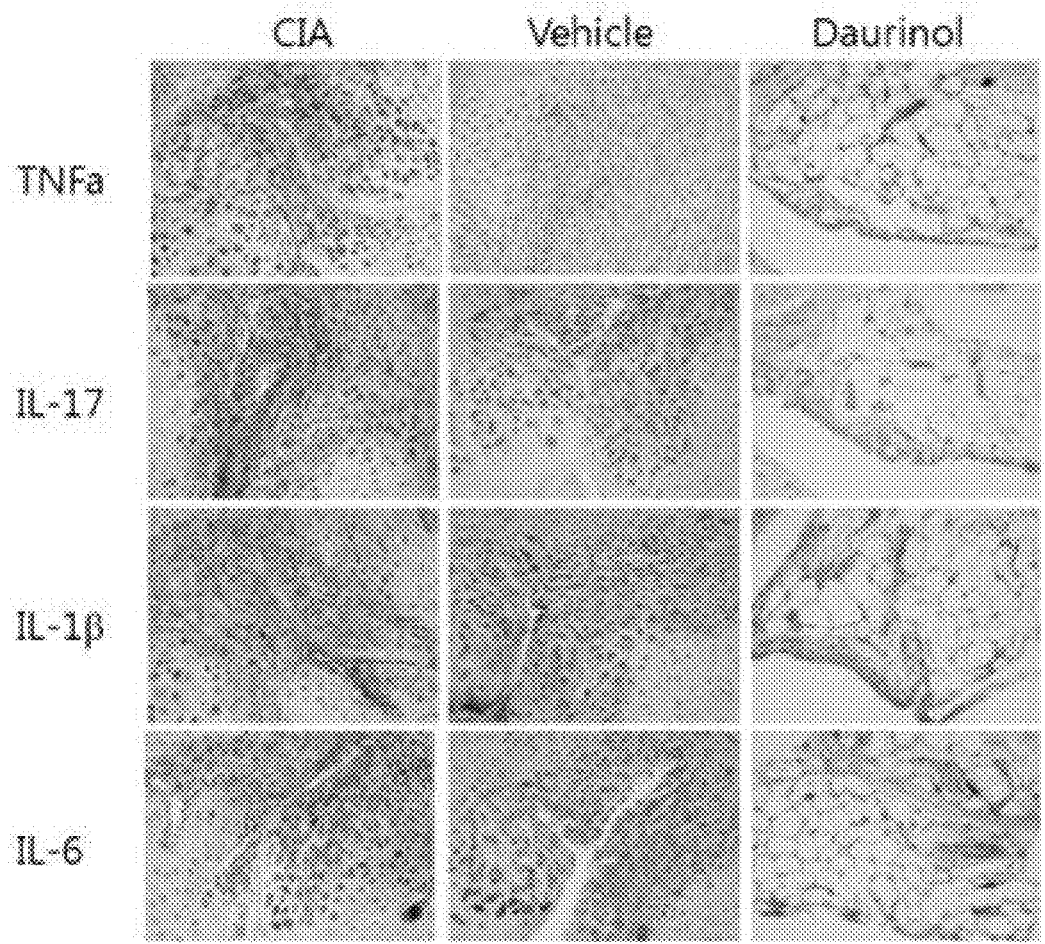
FIG. 4 illustrates the results of the changes in expression of IL-17, IL-6, IL-1beta, and TNF-α, which are inflammatory cytokines, observed after administration of daurinol in an animal model with arthritis.

As a result of confirming the expression of IL-17, IL-6, IL-1beta, and TNF-α, it was confirmed that the expression of IL-17, IL-6, IL-1beta, and TNF-α, which are inflammatory cytokines, was significantly increased in the joints of an animal model with arthritis. However, the expression levels of IL-17, IL-6, IL-1beta, and TNF-α were significantly reduced in the animal injected intravenously with daurinol (FIG. 4). Accordingly, it was confirmed that the daurinol of the present invention can significantly reduce the expression of inflammatory cytokines thereby capable of treating diseases.

<1-6> Analysis of Inhibitory Effect on the Differentiation of Osteoclasts

ICR mice (6 to 9 week-old male) were subjected to cervical dislocation and disinfected with 70% ethanol. The skin in the tibia area was cut off and the muscles attached thereto were detached. The distal center of tibia was cut off and tibia was ablated by dislocating patella. Both ends of the bone were slightly cut off and a 25G injection needle was indwelled therein on one end and α-MEM was flowed thereon and bone marrow cells were thereby collected into a test tube. After centrifugation, the resultant was suspended in α-MEM and red blood cells were removed by adding two volumes of Gey's solution. After centrifugation, the resultant was resuspended in α-MEM including 10% FBS and cultured to be used.

The cultured bone marrow cells were cultured overnight with macrophage colony stimulating factor ("M-CSF", hereinafter) (10 ng/mL), and the suspension cells were cultured further with M-CSF (30 ng/mL) for 3 days, and thereby bone marrow macrophages ("BMM") were formed. The thus-formed BMM was collected and cultured in $1 \times 10^5$ cells/well in the presence of receptor activator of NF-κB ligand (RANKL) (50 ng/mL), which is an osteoclast differentiation factor, and M-CSF (30 ng/mL) for 4 days. Upon completion of the cultivation, the cells were fixed with 10% formalin for 10 minutes, re-fixed with ethanol-acetone (1:1) for 1 minute, and stained with tartrate-resistant acid phosphatase (TRAP). The resultant was observed under a microscope and TRAP+ cells having three or more nuclei were determined as multinucleate osteoclasts.

Figure 5:
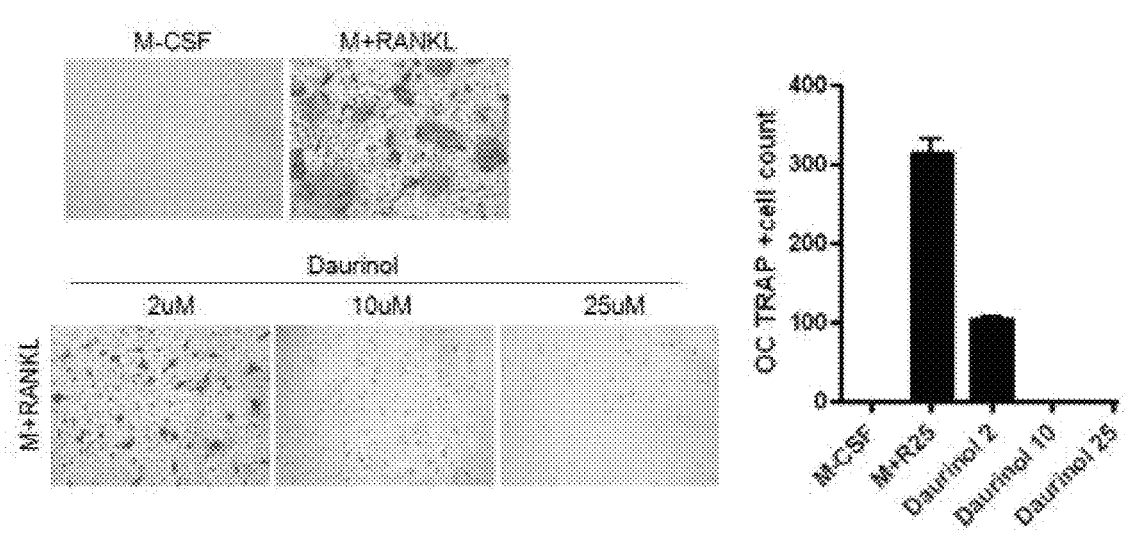
FIG. 5 illustrates the results of the degree of differentiation of osteoclasts observed after in vitro treatment with daurinol.

Upon measurement of the number of TRAP+ multinucleate cells (MNC), the differentiation of osteoclasts were reduced by 60% or more when they were treated with the daurinol compound (2 μM), while no differentiation of osteoclasts was observed when treated with the daurinol compound (10 μM), thus confirming that the daurinol compound inhibits the differentiation of osteoclasts in a dose-dependent manner (refer to FIG. 5).

Figure 6A:
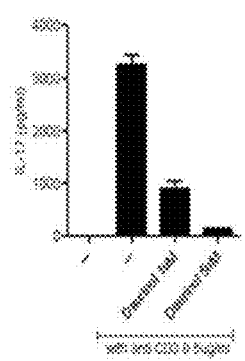
FIGS. 6A and 6B illustrate the results of the effects of daurinol in inhibiting inflammation and controlling the activity of Th17/Treg cells in an animal model with obesity arthritis.

<1-7> Examination of the Effects of Daurinol on the Inhibition of Inflammation and on the Control of the Activity of Th17/Treg Cells in an Animal Model with Obesity Arthritis The splenocytes of an animal model with obesity-derived rheumatoid arthritis were treated with daurinol (1 μM and 5 μM) and anti-CD3 (0.5 μg/mL), and IL-17, the inflammatory cytokine expressed thereafter, was evaluated via ELISA assay. As a result, it was confirmed that daurinol inhibits the expression of IL-17 in a dose-dependent manner (refer to FIG. 6A).

Figure 6B:
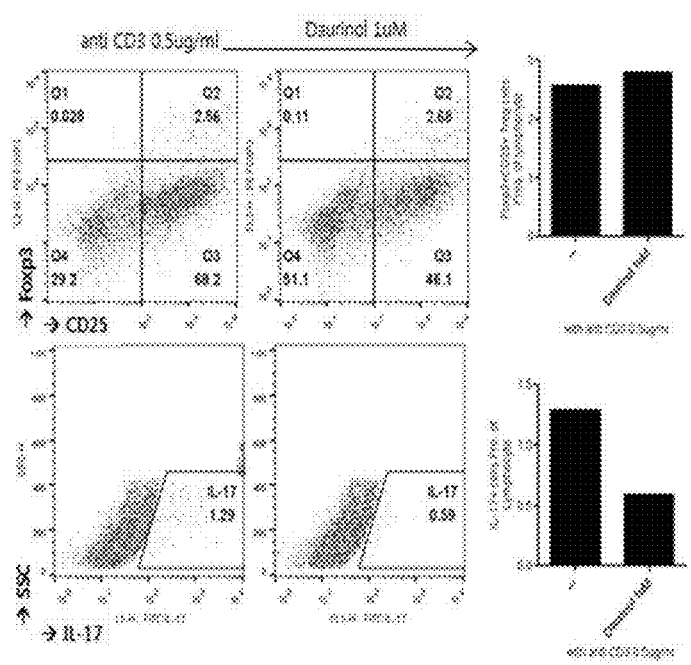

Additionally, for the confirmation of controlling the activity of Th17/Treg cells, the splenocytes of an animal model with obesity arthritis were treated with daurinol (1 μM) and anti-CD3 (0.5 μg/mL) and cultured for 3 days, and the activity of Th17/Treg cells controlled by daurinol were evaluated via flow cytometry. As a result, it was confirmed that daurinol significantly inhibited the expression of IL-17, which is expressed in an animal model with obesity arthritis, and simultaneously induced the activity of Foxp3+ Treg cells (refer to FIG. 6B).

EXAMPLE 2

Effect of Daurinol on the Inhibition of Inflammatory Cytokines and Measurement of Cytotoxicity Generally, the differentiation of osteoclasts is known to be promoted by secretion of inflammatory cytokines. In this regard, this example intends to identify the effect of the daurinol compound of the present invention on the secretion of inflammatory cytokines.

For this purpose, a splenocyte cell line was treated with anti-CD3 antibodies (0.5 μg/mL) to induce the secretion of IL-17, or treated with LPS (100 ng/mL) to induce the secretion of TNF-α. Then, the splenocyte cell line was treated with daurinol at concentrations of 0.5 μM, 2.5 μM, and 20 μM, and the supernatants were combined and the amount of IL-17 and TNF-α were examined by sandwich ELISA assay. The resultant was reacted in a 96-well plate with monoclonal anti-IL-17 or anti-TNF-α (2 μg/mL) at 4° C. overnight, and upon reaction, the non-specific binding was blocked using a blocking solution (1% BSA/PBST). IL-17 recombinant or TNF-α in a half amount was continuously diluted and used as standards, and the supernatant of cell culture was reacted at room temperature for 2 hours. Then, the biotinylated anti-IL-17 was reacted at room temperature for 2 hours, washed 4 times, and added with ExtraAvidin-alkaline phosphatase conjugate after dilution, and reacted at room temperature for 2 hours. Subsequently, PNPP/DEA solution was added thereto to fix color and absorbance was measured at 405 nm.

Figure 7A:
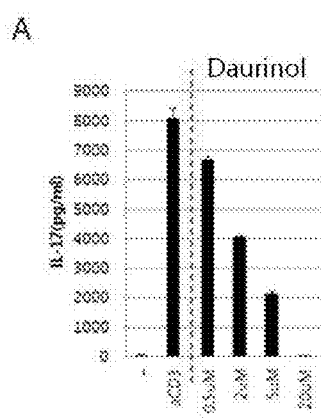
FIGS. 7A, 7B and 7C illustrate the observed results of the effects of in vitro daurinol treatment on the inhibition of IL-17 secretion (A), on the inhibition of TNF-α secretion (B), and the cytotoxicity according to daurinol concentration (C).
Figure 7B:
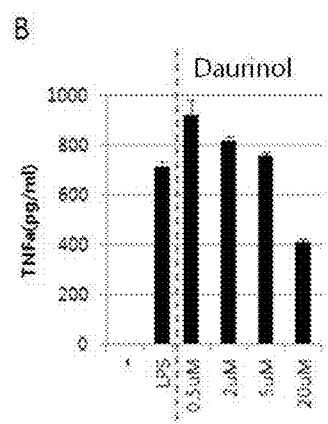
Figure 7C:
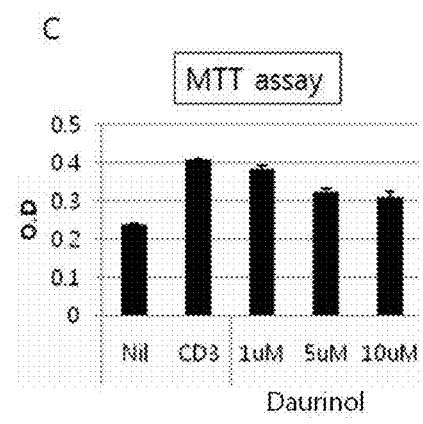

As a result, the secretion of IL-17 was exhibited to decrease in a dose-dependent manner according to the daurinol treatment; for example, the secretion was decreased to 50% when treated with 2 µM daurinol, while no secretion was observed when treated with 20 µM daurinol (refer to FIG. 7A). Meanwhile, the secretion of TNF-α was decreased by the daurinol treatment; for example, the secretion of TNF-α was decreased by about 40% when treated with 20 µM daurinol (refer to FIG. 7B).

Through the Examples above, the present inventors have confirmed that the daurinol compound of the present invention can inhibit the secretion of inflammatory cytokines thereby inhibiting the differentiation of osteoclasts, and as a result, exhibiting the therapeutic effect of treating arthritis.

Additionally, MTT assay was performed for the observation of cytotoxicity by daurinol treatment. To this end, splenocytes cell line ($2\times10^5$ cells) were plated on a 96-well plate, and daurinol was treated with MTT reagent and wrapped with aluminum foil, and reacted at 37° C. for 4 hours. After 4 hours, the crystals formed were dissolved in DMSO and the absorbance was measured using the ELISA reader. As a result, there was no significant cytotoxicity exhibited according to the concentration of daurinol (refer to FIG. 7C).

EXAMPLE 3

Measurement of the Inhibitory Effect on Phospho-STAT3 and Phospho-mTOR Signaling According to Treatment with Daurinol Compound For the observation of changes in intracellular cell signaling factors treated with daurinol, a western blot analysis was performed. For this purpose, CD4+T cells were isolated from a normal mouse, treated with daurinol (5 µM) in a condition already treated with anti-CD3 antibodies (0.5 µg/mL), cultured for 3 days, and the cells were dissolved and proteins were extracted therefrom. Then, the extracted proteins were subjected to SDS-PAGE electrophoresis, and the proteins were electrically transferred onto a nitrocellulose membrane, subjected to a blocking reaction with 5% skim milk for 1 hour, reacted by attaching primary antibodies to STAT3, STAT3p705, STAT3p727, and phospho m-TOR thereto, reacting again by attaching secondary antibodies to the same, and sensitized onto a Kodak X-ray using enhanced chemilunimoeence (ECL), and thereby the protein expression levels of the genes were analyzed.

Figure 8:
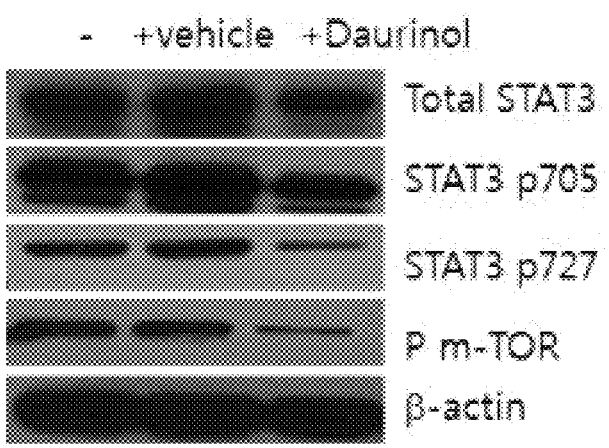
FIG. 8 illustrates the results of the effects of daurinol treatment on phospho STAT5 and phospho m-TOR signaling observed using daurinol-treated CD4+T cells.

As a result, the CD4+T cells treated with daurinol were exhibited to have a significant decrease in the expression of phospho STAT3 (p705, p'727) and phospho m-TOR (FIG. 8). This result suggests that the inhibition of mTOR-STAT3 activity caused by daurinol plays an important role in the inhibition of inflammation.

EXAMPLE 4

Analysis of the Effect of Daurinol on the Inhibition of Graft Versus Host Disease The present inventors have confirmed the effect of the daurinol compound on the treatment of arthritis as described above, and in this regard, they have examined the effect of the daurinol compound whether it can alleviate graft rejection, which is a different immune disease.

<4-1> Examination of Therapeutic Effect of Daurinol on Graft Versus Host Disease (GVHD)

In order to confirm whether daurinol can be actually applied to the treatment of a different immune disease, the therapeutic effects of daurinol was examined using an animal model with graft versus host disease. First, for the construction of an animal with graft versus host disease, a recipient mouse, Balb/c(H-2k/d), was exposed to total body irradiation (TBI) (800 cGy). Then, hematopoietic stem cells and splenocytes were isolated from the femur and the tibia of the donor mouse and the hematopoietic stem cells ($5\times10^6$ cells) and the splenocytes ($1\times10^6$ cells) were transplanted to a recipient mouse Balb/c(H-2k/d). After the transplantation, daurinol (20 mg/kg of weight) was injected 3 times a week for a total of 9 times, and in particular, daurinol was used after dissolving in a mixed solvent (DMSO:Cremophor EL:DW=1:1:8). The experiment was performed and analyzed for the experimental groups in which each group consisted of five mice.

Figure 9A:
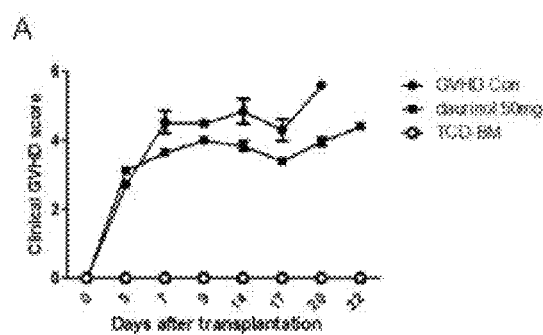
FIGS. 9A and 9B illustrate the results of the therapeutic effect of daurinol on graft versus host disease (GVHD) examined by measuring weight, degree of disease, and degree of survival of an animal model.
Figure 9B:
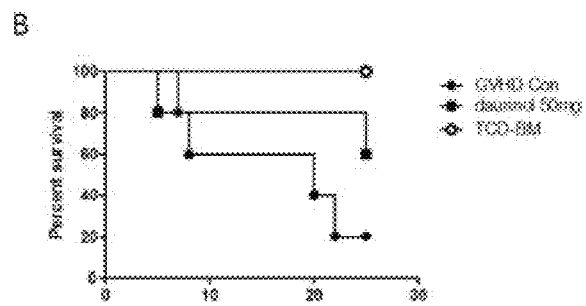

Upon measurement of the weight, degree of disease and observation of the degree of survival of the mice, the group of mice injected with daurinol exhibited an improvement in the degree of disease and the maintenance of the degree of survival for 30 days compared to that of the control group with graft versus host disease (refer to FIG. 9).

<4-2> Observation of the inhibition of T cell proliferation and the changes in the expression amount of IL-17 by daurinol treatment For the confirmation of the effect of the daurinol compound on the inhibition of T cell proliferation and the expression amount of IL-17, the CD4+ T cells ($2\times10^5$ cells) of a normal recipient (Balb/c, responder), and the T cell-removed splenocytes ($2\times10^5$ cells) derived from a recipient (homogenic) or the splenocytes ($2\times10^5$ cells) derived from a donor (C57BL/6, stimulator, allogenic) exposed to irradiation were added to each well of a 96-well round bottom plate, mixed, and cultured in vitro. In particular, the T cell proliferation and the secretion of IL-17 when an allogenic reaction was untreated with daurinol or treated with daurinol at 0.5 µM, 2 µM, 10 µM, and 20 µM, respectively, were observed.

As a result, it was confirmed that daurinol inhibited T cell proliferation in a dose-dependent manner (refer to FIG. 10), and also inhibited the expression of IL-17 (refer to FIG. 11). Accordingly, it was confirmed that daurinol has the effect of inhibiting the graft rejection.

<4-3> Observation of the Differentiation Features of Regulatory T Cells by Daurinol Treatment Meanwhile, regulatory T lymphocytes (Treg) are known to play a crucial role in maintaining immunological tolerance (Nat. Rev. Immunol. 2009, 7:305), and require the expression of Foxp3, which is a transcription factor mainly produced in the thymus, and Foxp3 is known to play a role in the inhibition of inflammatory cytokines production.

In this regard, for the confirmation of the effect of the daurinol compound according to the present invention on the activity of regulatory T lymphocytes (Treg), the present inventors analyzed the T cells isolated in Example <4-2> by a flow cytometer. That is, the T cells isolated in Example <4-2> were collected, washed with the FACs buffer, and reacted at 4° C. for the blocking of nonspecific binding for 5 minutes, and washed with the FACs buffer. Anti CD4 percp cy5.5 and anti CD25 APC were added thereto and reacted at 4° C. for 30 minutes, and washed with the FACs buffer. Then, the cytoperm/cytofix buffer (100 μL each) was added and reacted at 4° C. for 30 minutes, and washed with the perm wash buffer. A blocking reaction was performed at 4° C. for the prevention of nonspecific binding for 15 minutes, and washed with the perm wash buffer. Meanwhile, Anti Foxp3 PE was added thereto and reacted at 4° C. for 30 minutes, and washed with the perm wash buffer. Upon staining of the cells, the cells were washed with buffer and analyzed using the fluorescent-activated cell sorter (FACs).

As a result, the group treated with daurinol (1 μM) of daurinol exhibited 9.18% of Treg cells and the group treated with daurinol (5 μM) of daurinol exhibited an increase of Treg cells to 16.6%, compared to 7.27% of Treg cells in the control group not treated with daurinol, thus confirming that daurinol inhibits the graft rejection by inhibiting the expression of Treg (refer to FIG. 12).

EXAMPLE 5

Analysis of the Effect of Daurinol on the Treatment of Inflammatory Bowel Disease <5-1> Construction of an Animal Model with Inflammatory Bowel Disease (IBD)

For the confirmation of the effect of the daurinol compound of the present invention on the treatment of inflammatory bowel disease, the present inventors first constructed an animal model with induced inflammatory bowel disease. For the experimental model, C57BL/6(H-2kb) mice were used. For the construction of an animal model with induced inflammatory bowel disease, the mice were fed with 3.5% dextran sulfate sodium (DSS) and water for a week, thereby preparing an animal model with induced inflammatory bowel disease.

<5-2> Observation of Weight, Severity of Disease Activity Index, and Length of Intestine of an Animal Model with Inflammatory Bowel Disease by Daurinol Treatment The present inventors divided the experimental animals into a normal control group, a group of an animal model with induced inflammatory bowel disease, and a group of an animal model with induced inflammatory bowel disease treated with daurinol or a TNF-α inhibitor, and the group treated with daurinol was administered orally and intrarectally with daurinol (20 mg/kg) from the $4^{th}$ day after the induction with the disease.

As a result, the group treated with daurinol exhibited a significant improvement in weight compared to that of the group with induced inflammatory bowel disease, and their weight was exhibited to become similar to that of the control group with time, and the group treated with daurinol was confirmed to maintain their weight more similarly to that of the animal model with inflammatory bowel disease compared to the TNF-α inhibitor, and also confirmed to inhibit and control the disease (refer to FIG. 13A).

Then, upon evaluation of the degree of activity of inflammatory bowel disease (weight, degree of thickness of feces, and bleeding), the group treated with daurinol exhibited a significant decrease in disease activity index (DAI), thus confirming that daurino can significantly inhibit the activity of inflammatory bowel disease (refer to FIG. 13B).

Additionally, one of the features of inflammatory bowel disease is that the damage and shortening of the length of the large intestine are related to the disease activity index. For the analysis of the therapeutic effect of daurinol on the inflammatory bowel disease, the experimental animals were euthanased two weeks after the daurinol treatment, and the length of their intestines were measured. As a result, it was confirmed that the group treated with daurinol exhibited a significant increase in the length of the intestine compared to that of the animal model with inflammatory bowel disease thus exhibiting the intestinal length being close to that that of the normal control group (refer to FIG. 13C).

Additionally, for the confirmation of the histological findings of the tissues in the large intestine and the expression of inflammatory cytokines, a hematoxylin and eosin (H&E) staining was performed to examine whether the damage of the tissues in the large intestine was reduced by the daurinol treatment. As a result, it was confirmed that the animal model with inflammatory bowel disease (IBD) exhibited serious damages of the tissues in the large intestine, whereas the group treated with daurinol exhibited a decrease in the intestinal tissue damage, relatively. Additionally, it was also confirmed that the daurinol treatment significantly inhibits the expression of inflammatory cytokines TNF-α (refer to FIG. 13D).

<5-3> Measurement of Reduction in Secretion of Inflammatory Cytokines in the Intestinal Tissues and the Inhibition of Expression of Mouse/Humans VEGF by Daurinol Treatment Upon confirmation of the expression of inflammatory cytokines in the tissues of the large intestine, daurinol was exhibited to significantly inhibit the expression of TNF-α, IL-6, IL-8, IL-1b, and IL-17, which are the inflammatory cytokines related to inflammatory bowel disease, in the tissues of the large intestine (refer to FIG. 14A).

Additionally, upon examination of the VEGF expression in the intestinal tissues, it was confirmed that daurinol significantly inhibited the VEGF expression in the intestinal tissues of an animal (mouse) model with inflammatory bowel disease (refer to FIG. 14B). Upon evaluation of the effect of daurinol using human large intestine cell line HT-29 cell line whether daurinol can inhibit and control the expression of VEGF, which is expressed in the cell line of the human large intestine, it was confirmed that daurinol has a greater inhibitory effect against the VEGF expression compared to those of TNF-α inhibitor and merformin. Additionally, upon analysis in terms of inhibition (%), it was confirmed that daurinol significantly inhibits the activity of VEGF (refer to FIG. 14C).

<5-4> Examination of Changes in Inflammatory Cytokines and Antibody Formation in the Serum of an Animal Model with Inflammatory Bowel Disease Sera were isolated from a mouse with induced inflammatory bowel disease (IBD), and mice treated with daurinol and TNF-α inhibitor, respectively. The levels of IL-17, IFNγ, IL-6, and the like, which are inflammatory cytokines, in the isolated sera were measured by ELISA assay. As a result, it was confirmed that daurinol significantly inhibits the expression of these inflammatory cytokines (refer to the upper graphs of FIG. 15).

Figure 15:
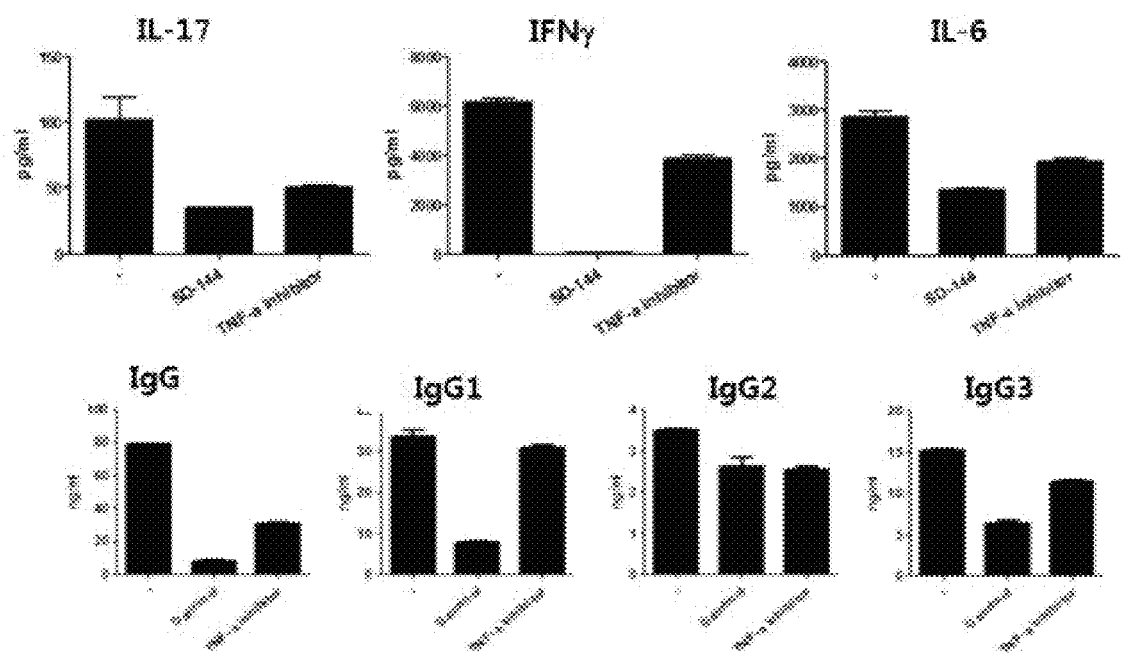
FIG. 15 illustrates the measurement results of the effects of daurinol treatment on the changes in the expression of inflammatory cytokines (IL-17, IFNγ, and IL-6) (the top graphs) and the changes in production of antibodies (IgG, IgG1, IgG2, and IgG3), in the serum of an animal model with inflammatory bowel disease.

Additionally, upon measurement of the antibodies expressed in the sera, it was confirmed that daurinol reduced the levels of IgG, IgG1, IgG2, and IgG3 antibodies (refer to the lower graphs of FIG. 15). Accordingly, since daurinol can reduce not only the expression of the inflammatory cytokines but also the formation of antibodies in an animal model with inflammatory bowel disease, daurinol can inhibit and control the immune response to autoantibodies and the B cell-related inflammation responses.

EXAMPLE 6

Analysis of the Effect of Daurinol on the Treatment of Lupus

For the confirmation of the effect of daurinol of the present invention whether daurinol has the therapeutic effect on the treatment of another immune disease, lupus (SLE), the effects of inhibiting inflammation and controlling the activity of Th17/Treg cells in an animal model with lupus were examined.

First, regarding the effect of controlling the autoantibody formation, the splenocytes of an animal model with lupus were treated with daurinol (1 μM and 5 μM) and LPS (100 ng/mL) for three days and the levels of IgG antibodies expressed thereof were evaluated by ELISA assay. As a result, it was confirmed that daurinol inhibited the formation of IgG antibodies in a dose-dependent manner (refer to FIG. 16A).

Additionally, for the confirmation of the effect of controlling the formation of inflammatory cytokines, the splenocytes of the animal model with lupus were treated with daurinol (1 μM and 5 μM) and anti-CD3 (0.5 μg/mL) or LPS (100 ng/mL) for three days and the levels of IL-17 and TNF-α inflammatory cytokines were evaluated by ELISA assay. As a result, it was confirmed that daurinol inhibited the expression of IL-17 and TNF-α in a dose-dependent manner, and in particular, daurinol has an excellent inhibitory effect against IL-17 (refer to FIG. 16B).

Finally, for the confirmation of the controlling the activity of Th17/Treg cells, the splenocytes of an animal model with lupus were culture for three days after treating with daurinol (1 μM) and anti-CD3 (0.5 μg/mL), and the activity of Th17/Treg cells being controlled by daurinol was evaluated by flow cytometry. As a result, it was confirmed that daurinol can not only inhibit the Th17 activity expressed in an animal model with lupus but also simultaneously induce the activity of Foxp3+ Treg cells (refer to FIG. 16C).

The present invention has been explained referring to exemplary embodiments. Those of ordinary skill in the art will recognize that the present invention may be embodied in other specific forms without departing from its spirit or essential characteristics. The described embodiments are to be considered in all respects only as illustrative and not restrictive. The scope of the present invention is, therefore, indicated by the appended claims rather than by the foregoing description. All changes which come within the meaning and range of equivalency of the claims are to be embraced within the scope of the present invention.

The invention claimed is:

1. A method for treating immune diseases comprising administering to a patient in need thereof an effective amount of daurinol represented by the following Formula 1:

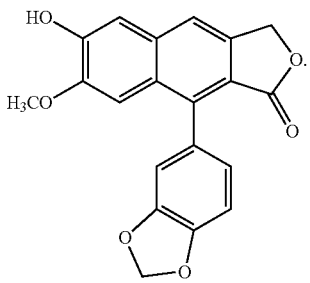

[Formula 1]

wherein the immune disease is post transplantation late and chronic solid organ rejection, inflammatory bowel disease, systemic lupus erythematosus, osteoarthritis, or rheumatoid arthritis.

2. The method of claim 1, wherein the daurinol is separated from an extract of a plant belonging to *Haplophyllum* species.

3. A method of controlling secretion of inflammatory cytokines in a patient suffering from immune diseases comprising administering to the patient in need thereof an effective amount of daurinol represented by the following Formula 1:

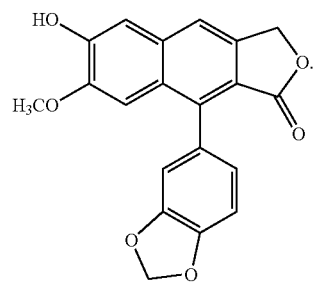

[Formula 1]

4. The method of claim 3, wherein the inflammatory cytokines are IL-17 or TNF-α.

5. The method of claim 1, wherein the daurinol exhibits one or more effect selected from inhibition of the differentiation of osteoclasts, reduction of intraarticular inflammation, reduction of osteoclasia and reduction of cartilage damage.

6. The method of claim 1, wherein the daurinol exhibits one or more effect selected from inhibition of proliferation of alloreactive T cells and increase of expression of Regulatory T cells (Treg).

7. The method of claim 3, wherein the immune diseases are any one selected from the group consisting of post transplantation late and chronic solid organ rejection, inflammatory bowel disease, systemic lupus erythematosus, osteoarthritis, and rheumatoid arthritis.

* * * * *